United States Patent [19]

Baba et al.

[11] Patent Number: 4,794,257

[45] Date of Patent: Dec. 27, 1988

[54] QUANTUM-COUNTING RADIOGRAPHY

[75] Inventors: Sueki Baba, Suita; Osamu Yamamoto, Moriguchi; Tadaoki Yamashita, Hirakata; Hiroshi Tsutsui, Yawata, all of Japan

[73] Assignee: Matsushita Electric Industrial Co., Ltd., Kadoma, Japan

[21] Appl. No.: 610,805

[22] Filed: May 16, 1984

[51] Int. Cl.⁴ .............................................. G01T 1/24
[52] U.S. Cl. .............................................. 250/370.01
[58] Field of Search ................... 378/146; 250/370 G, 250/370 J, 370 H

[56] References Cited

U.S. PATENT DOCUMENTS

| | | | |
|---|---|---|---|
| 3,937,965 | 2/1976 | Vasseur | 250/366 |
| 3,975,637 | 8/1976 | Ikedo et al. | 250/327.2 |
| 4,174,481 | 11/1979 | Liebetruth | 378/20 |
| 4,255,659 | 3/1981 | Kaufman | 250/370 G X |
| 4,366,574 | 12/1982 | Hill | 378/146 |
| 4,651,005 | 3/1987 | Baba et al. | 250/370 G X |

FOREIGN PATENT DOCUMENTS

| | | | |
|---|---|---|---|
| 132382 | 7/1984 | Japan | 250/370 G X |
| 2017295 | 3/1978 | United Kingdom | |

OTHER PUBLICATIONS

Akad'eva et al., "Spectrometric Gamma Quantum Detectors Using Cadmium Telluride Crystals", Sov. Phys. Dokl, 20(3), 1975, pp. 211-213.

Krapivin et al., "Pulse Selection to Improve Energy Resolution of γ Spectrometers with Cadmium Telluride Detectors", Atomic Energy, 43(1), Jul. 1977 pp. 633-636.

Naruse et al., "Multichannel Semiconductor Detectors for X-Ray Transmission Computed Tomography", IEEE Transactions on Nuclear Science, vol. NS-27, No. 1 Feb. 1980, pp. 252 to 257.

Primary Examiner—Carolyn E. Fields
Attorney, Agent, or Firm—Cushman, Darby & Cushman

[57] ABSTRACT

A radiation quantum-counting method and apparatus for producing high resolution radiographic images capable of discriminating soft tissue cancer having a 1cm size. The high resolution image is generated by a plurality of radiation sensitive elements, each element including a semiconductor material having a pair of electrodes mounted on opposite faces thereof. Each element is highly sensitive and produces a rapid pulse count since the thickness of the semiconductor material is substantially 0.1–0.5 mm, and the semiconductor material has an effective atomic number greater than 30 and an energy band gap greater than 1.3 eV. As a plurality of radiation quanta emanate from the radiation source, they are received by the plurality of radiation sensitive elements which detect individual radiation quantum and produce a pulse signal for each detected quantum. Coupled to each radiation sensitive element is a pulse amplifier for amplifying the pulse signals. The amplified pulse signals are counted and used to produce radiographic image signals containing details of image gradation. The pulse count may also be stored in a memory and used to provide two-dimensional information when combined with other pulse count data derived when the spatial orientation between the objective body and the radiation source is changed.

11 Claims, 9 Drawing Sheets

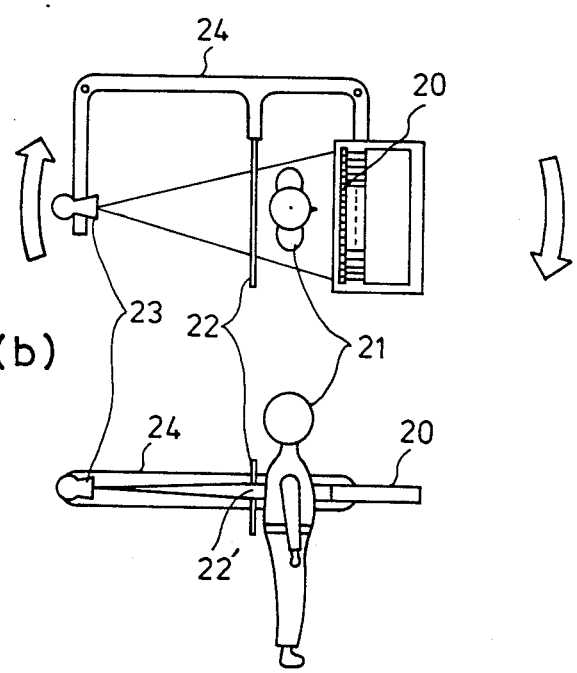

QUANTUM-COUNTING RADIOGRAPHY

BACKGROUND OF THE INVENTION

1. Field of the Invention

The present invention relates generally to a method of conducting radiography and apparatus for carrying out the radiography. Particularly, the present invention concerns quantum-counting radiography suitable for diagnosis or non-destructive examination and apparatus for carrying out such radiography.

2. Description of the Prior Art

Hitherto, radiographic recording examination or observation (with X-ray, or the like) using high energy radiation, silver salt photographic film or image intensifiers or the like apparatus have been used to improve image quality. Other various proposals have been made to provide higher quality image productions.

Thermo-luminescent film (for instance, disclosed in the Japanese examined patent publication No. Sho 55-47720) and methods of using optical stimulated luminescent film (disclosed in the Japanese unexamined patent publication No. Sho 55-15025) have been proposed such that high sensitivity and wide dynamic ranges are expected, but these conventional proposals fail to attain instantaneous reproduction of an image. As a known system, the CT/T Scout View System for obtaining two-dimensional images of the objective body utilizes a radiation detector array and moves the objective body in relation to the radiation detector array. Such a system has been manufactured and sold by General Electric Company Ltd. of the United States. The system comprises a xenon gas detector having 511 channels as the radiation detector array for reading out the electric charge corresponding to radiation intensity of each detector to produce the image. However, the system has poor sensitivity in the detectors and accordingly the object body must receive large radiation exposure, and it is impossible to improve resolution because of loss of sensitivity when the detector is adapted to a small size.

SUMMARY OF THE INVENTION

Accordingly, the purpose of the present invention is to provide an improved apparatus and method of radiography which has high sensitivity as well as high resolution in an instantaneous production of a two dimensional image.

The quantum-counting method of radiography in accordance with the present invention includes the following steps:

(a) emitting radiation from a radiation source, (b) receiving the radiation which penetrated through the objective body on a linear array of radiation sensitive elements, and (c) moving the relative spatial relation of the radiation source and the radiation sensitive element with respect to the objective body, thereby to induce signals containing two-dimensional radiographic information, characterized in that the radiation sensitive elements comprise semiconductor elements which simultaneously receive the radiation rays and detect the radiation as pulse number rates of the quantum of radiation, output signals of respective radiation sensitive elements are amplified by corresponding pulse amplifiers and counted by subsequent pulse counters connected thereto, to produce radiographic image signals, wherein gradations of the image are given from the pulse counter as pulse number data, the pulse number data given from the pulse counter are given to memory means, then, after the changing of the relative spatial relation of the radiation source and the radiation sensitive element with respect to the objective body, the above-mentioned procedures are sequentially repeated with cooperative gradual changing of the relative spatial relation, thereby to produce a two-dimensional signal of quantum number data of gradation.

Also the apparatus for quantum-counting radiography in accordance with the present invention comprises:

(a) a radiation source for emitting radiation, (b) a linear array of radiation sensitive element for receiving radiation which penetrates through the objective body, (c) means for changing the relative spatial relation of the radiation source and the radiation sensitive element with respect to the objective body, thereby to induce signals containing radiographic information with respect to different relative spatial relation, characterized in that each of the radiation sensitive elements comprises a semiconductor element to receive the radiation rays and, the quantum counting radiography apparatus comprises (i) pulse amplifiers respectively connected to corresponding ones of the radiation sensitive elements, (ii) pulse counters respectively connected to corresponding ones of the pulse amplifiers to issue corresponding pulse number data therefrom, (iii) memory means for storing the pulse number data, and (iv) controlling means for making the memory store a sequence of the pulse numbers after respective changes in the relative spatial relation.

For instance, the above-mentioned radiation source emits radiation, (for instance, X-rays in at least a fan-shaped emission), and the radiation sensitive element which receives the radiation is disposed in a line or in an arc shape, so that the objective body such as a human body or some machine to be non-destructively examined is placed between the source and the receiving elements. The radiation sensitive element is made of some semiconductor. Appropriate semiconductor materials for the radiation sensitive element include CdTe and GaAs. Radiation is read out by being converted into discrete pulses, and is amplified by pulse amplifiers, and the amplified pulses are counted by pulse counters. That is, for each radiation sensitive element, one pulse amplifier and one pulse counter are provided thereby to simultaneously count the amount of radiation incident on a multiplicity of radiation sensitive element arrays. The counted pulse numbers per predetermined unit time, namely pulse rates, are sent to respective addresses of a memory. Then, the radiation source and the array of the radiation sensitive elements are displaced with respect to the objective body, for instance, continuously, or step by step with a small displacement. And after moving to a new position, the same procedures are sequentially repeated many times. Thus two-dimensional radiological information with respect to the objective body is obtained.

By using semiconductor material as the radiation detector together with the below-mentioned features, an extremely high sensitivity is obtainable, in comparison with conventional system. Each semiconductor detector element issues one electric pulse for one quantum radiation absorbed by the semiconductor detector. Accordingly, in principle there is no other method which gives higher sensitivity than this. This invention can attain high sensitivity by providing a number of minutely configurated semiconductor radiation sensitive elements, and by counting the high speed pulse train in parallel by using a number of pulse amplifiers and a number of pulse counters, thereby attaining high sensitivity as well as high speed detection which can reduce radiation exposure.

Furhermore, the present invention can achieve high dynamic range because pulse counting is used for radiation detection. Therefore, by taking advantage of the large dynamic range, the finding of delicate differences in absorption between various soft tissues of the human body, (for instance, between muscle and fat) becomes possible. Thus, extensive use of CT scanners for detecting cancer becomes possible.

BRIEF DESCRIPTION OF THE DRAWING

FIG. 14(a) is a plan view showing an example of a computer tomography apparatus applying the present invention.

FIG. 14(b) is a side view of the embodiment of FIG. 14(a).

DESCRIPTION OF PREFERRED EMBODIMENT

Figure 1:
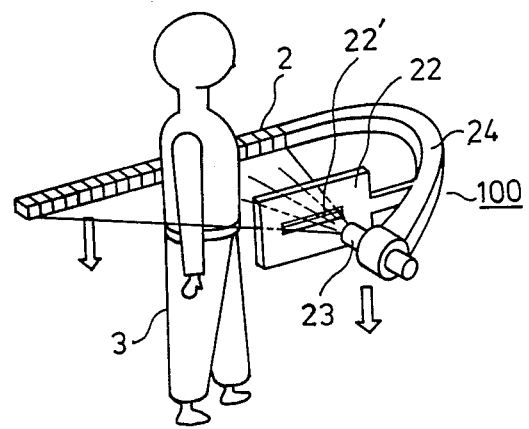
FIG. 1 is a perspective view showing an outline configuration of the quantum counting radiography apparatus of the present invention.

FIG. 1 is a perspective view of one example of the present invention wherein a radiation source 23, (for instance, an X-ray source), and an array of radiation sensitive elements 2, (such as CdTe semiconductor detectors) are mounted on a frame 100. A slit 22' is provided in front of the radiation source 23 so as to form the radiation rays in a fan-shape, and the array of radiation sensitive elements 2 is disposed on the plane of fan-shape radiation rays to receive them. The objective body 3 (such as a human body) is disposed between the slit 22' and the array 2 of the radiation sensitive elements. In this embodiment, the assembly comprising the radiation source 23, the array 2 of radiation sensitive elements, the slit plate 22 having the slit 22', and the arm 24 holding the above-mentioned components in one fixed relation, is slowly (or stepwisely with small increments) moved upward or downward.

Figure 2:
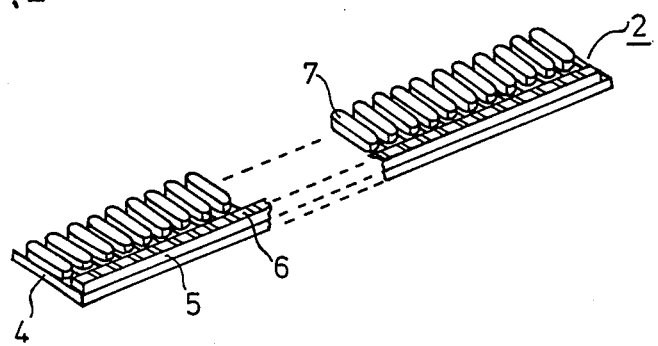
FIG. 2 is a perspective view showing an array of semiconductor detector elements, together with an array of pulse amplifiers and an array of pulse counters.

FIG. 2 is an enlarged perspective view of the array of radiation sensitive elements wherein, on a printed circuit substrate 4, an array 5 of detection elements made of semiconductor crystal material is disposed, and thereon electrodes 6 are disposed on respective picture element parts of the semiconductor detector. On the substrate 4, pulse amplifiers 7 are disposed and connected to corresponding electrodes 6 so as to amplify pulse signals output from respective semiconductor detectors. As the semiconductor detector material, various semiconductors may be considered. Hitherto, for such a semiconductor detector, silicon crystal or germanium crystal has been used. However, the use of CdTe or GaAs crystal as the material of the semiconductor detector element is one important feature of the present invention. The single crystal of such material is cut into a bar of about 0.5 mm thickness, about 1 mm width and 10–20 mm length, and the surface is ground smoothly and etching is performed thereon. And further thereon, the electrodes 6 and an opposite electrode are formed by known methods of vapor depositing gold or the like. The front side electrodes 6 are formed in a predetermined number, like islands on the top surface of the longitudinal crystal bar, and the opposite electrode (not shown) is formed as a continuous element on the lower surface of the crystal bar which is to contact the surface of the substrate 4. Alternatively, the opposite side electrode may be formed discretely in islands-shape in a manner similar to the top electrodes 6. A predetermined DC voltage is applied across the top side electrodes 6 and the opposite side electrode(s) so that predetermined DC electric fields are generated in the semiconductor detectors. As a modified example, comb shaped electrodes may be used. As still another modification, the single crystal may be cut into individual parts of picture elements which are provided each with a pair of electrodes on opposite sides. Such a structure may be used to form the array of semiconductor detectors.

As the semiconductor material for the single crystal of the semiconductor detectors, a semiconductor having a detection atomic number of over 30, and having an energy band gap of over 1.3 eV is suitable. Furthermore, the gap between the opposite electrodes of each semiconductor detector, namely the thickness of the semiconductor material, is preferably under 0.5 mm.

In order to improve contrast and resolution of the obtained range, it is naturally preferable that as many pulse numbers as possible are obtained from each picture element at each reception of the radiation. In order to achieve this, it is necessary that the pulse width of each detected pulse is as small as possible, thereby to enable counting of as many pulse numbers as possible within a predetermined time interval. In order to realize the above, it is necessary to decrease the thickness of the semiconductor crystal of the detector element so as to shorten the transit time of holes in the semiconductor crystals. Since the pulse width is proportional to the square of the thickness, (an actually sufficient small thickness is about 0.5 mm), and with a thickness of such or smaller figure, satisfactory reproduced images of high quality are obtainable by counting $10^5$–$10^6$ counts per picture element. On the other hand, when the semiconductor crystal is thin, the absorption rate of the X-rays is poor. When a material having an effective atomic number of over 30 with respect to photoelectric absorption is selected an absorption rate of about 30% is obtainable for about 0.5 mm thickness. That is, by selecting the above-mentioned conditions, a high sensitivity and high resolution imaging for radiography is obtainable with semiconductor detectors.

Figure 3:
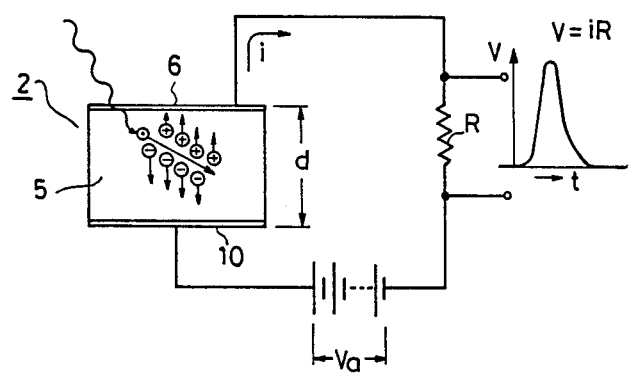
FIG. 3 is a circuit diagram of a semiconductor detector element showing the generation of the pulse in response to receiving one quantum of the radiation.

Hereafter, details of a high speed method of pulse counting radiation quantum by using the semiconductor detectors will be described. The principle of the present invention is elucidated in an example where the radiation is X-rays. The radiation incident on the crystal semiconductor of the detectors causes a photoelectric effect or Compton effect in the semiconductor material thereby generating secondary electrons. The secondary electrons move in the semiconductor crystal and generate electron-hole pairs along their path. The number of such electron-hole pairs is proportional to the initial energy of the secondary electrons. As shown in FIG. 3, when a strong electric field is generated in the semiconductor crystal of the crystal detector by connecting the top side electrode 6 and the bottom side electrode 10 across a potential source Va in series with a resistance load R, the electrons and the positive holes respectively move towards the bottom electrode 10 and the top side electrode 6 with a high speed, and thus generate electric charge pulses. The time between the reception of the radiation to the generation of the secondary electrons and the further generation of electron-hole pairs is very short, for instance, about $10^{-12}$ sec. However, since the transit time for the electrons and holes, (especially the latter) moving in the semiconductor crystal takes a relatively long time, it was hitherto impossible to obtain a high speed pulse output having very narrow pulse widths. In order to obtain an X-ray image of a human body, for instance, the composite structure of the X-ray source and the radiation sensitivity element array must be moved within a short time period (about 10 sec), during which more than 100 positions measuring data from the radiation sensitive element array must be read out. Therefore, one measuring time for each detection element must be smaller than 100 m.sec. When the pulse width is broad, the number of pulses that can be counted in this measuring interval is very small, thereby decreasing the dynamic range for each picture element, and also lowering the accuracy of the counting measurement. Accordingly, in order to improve counting accuracy, the pulse width must be made as narrow as possible, namely the pulses must be made high speed pulses. Hitherto, because of this problem the pulse counting measurement method has not been utilized, but instead a galvanometric method of measurement has been used (for instance, see, Y. Naruse et al., IEEE Trans. NS-27(1), p. 252, 1980). Besides, since the galvanometric measuring method measures the time-mean value of electric-charge pulses of radiation quantums, the accuracy of the radiation detection in low dose regions has been more than two digits smaller than that of the pulse counting method.

Figure 4A:
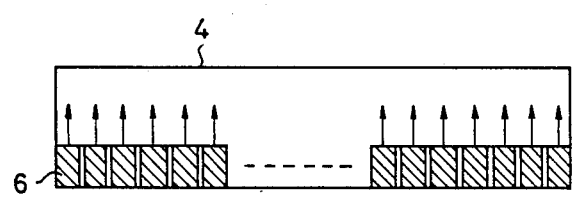
FIG. 4(a) is a schematical plan view of the radiation sensitive element array.
Figure 4B:
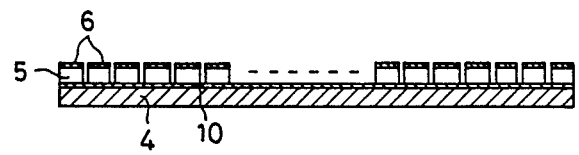
FIG. 4(b) is front view of the radiation sensitive array of FIG. 4(a).

One of the important features of the present invention is that in order to measure the pulse number, the radiation sensitive element, i.e., semiconductor crystal chips 5 are formed very thin, as shown in FIG. 4. And an opposite faces of each semiconductor crystal chip 5, a pair of electrodes, namely, top electrode 6 and bottom electrode 10 are formed. The bottom electrode 10 may be formed commonly to all semiconductor crystal chips. By selecting the very thin thickness of the semiconductor crystal chips, transit times of the electrons and positive holes to the electrodes 6 and 10 are much decreased, thereby producing very narrow pulses, and hence a high speed pulse train is obtainable. This point is described further in detail with reference to FIG. 3. Electron-hole pairs generated by radiation quantum receive the effect of the electric field applied to the semiconductor crystal through the application of a potential between the electrodes 6 and 10. As a result, the electrons are attracted to anode 10 and the positive holes are attracted to cathode 6, respectively. Therefore, a pulse current is generated in the external circuit which circuit comprises the resistor R and the potential source Va. And the pulse width t of the pulse signal is given by the following known equation:

$$t = d^2/\mu \cdot V_a \quad (1)$$

wherein t is the pulse width time, d is the distance across the two opposite electrodes on the semiconductor crystal chip, $\mu$ is the mobility of electrons or positive holes, and $V_a$ is the potential applied across the two opposite electrodes on the semiconductor crystal chip.

According to the above-mentioned equation, pulse width time t is proportional to the square of the thickness of the semiconductor crystal chip, and accordingly when the thickness is reduced, by a factor of 10 the pulse width is reduced by a factor of 100.

Figure 5:
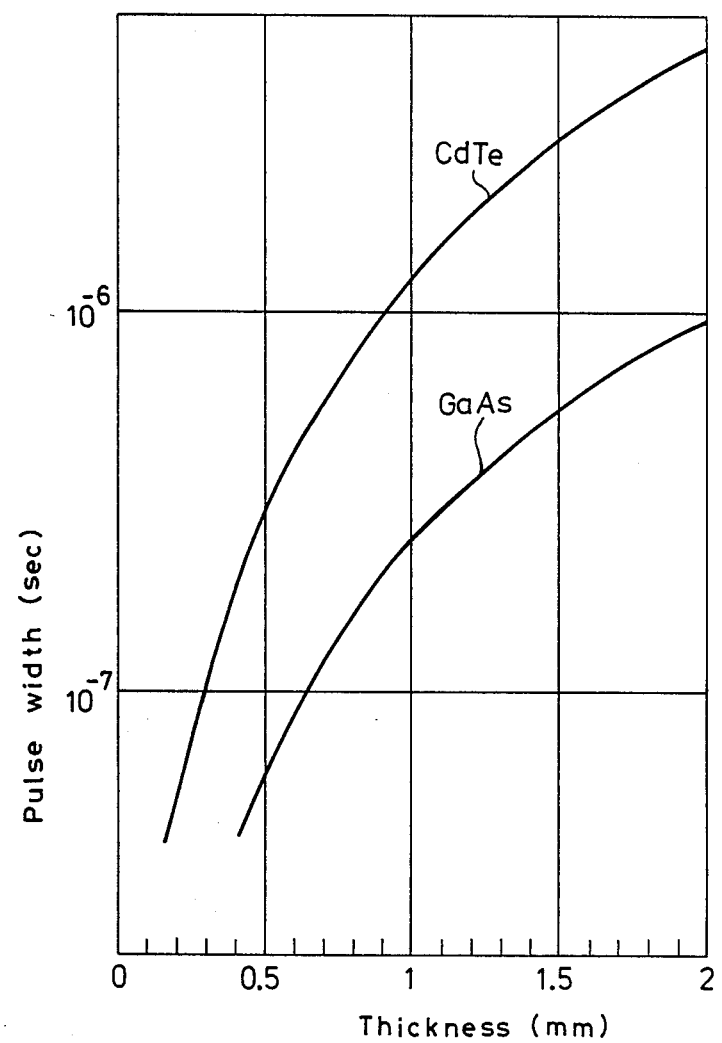
FIG. 5 is a graph showing relations between the thickness of one semiconductor element body of the radiation sensitive element and pulse width of the output signal therefrom.

Now, let us examine actual examples utilizing CdTe which has an effective atomic number of $Z_E=49$, and GaAs which has an effective atomic number of $Z_E=31$. Hole-mobility $\mu_n$ of $CdTe = \mu_h = 80$ cm$^2$/V·sec, and hole-mobility $\mu_h$ of GaAs is $\mu_h = 400$ cm$^2$/V·sec. A voltage of 100 V is applied across the electrode, and the pulse width for various thicknesses of semiconductor crystal are plotted in FIG. 5. For a 1 mm thickness of the semiconductor crystal chip, the pulse width of CdTe is 1$\mu$ sec and that of GaAs is 0.25$\infty$ sec. When the thickness of the semiconductor crystal chip is 0.5 mm, the pulse width of CdTe becomes 0.3$\mu$ sec and that of GaAs becomes 0.06$\mu$ sec. When compared, it is obvious that for a difference in the thickness between 1 mm and 0.5 mm, the pulse width differs by several times. Thus for a thickness of under 0.5 mm, the pulse width is below 0.3$\mu$ sec. This pulse width is substantially the narrowest one which can be achieved by actually usable modern circuit technology. Now, provided that the pulse integration time for one picture element is 100 m sec, the number of 0.1μ sec width pulses in 100 m sec becomes (100 msec→0.1μsec=)$10^6$. When the pulses are random pulses, error due to statistical fluctuation is $\sqrt{10^6}=10^3$, and measurement error for the picture element becomes 0.1%. It is generally known that differences in the diagnosis X-ray absorption coefficient between soft tissues (such as muscle, fat, and substantial water) are below several percent, and hence, in order to detect such slight differences measurement accuracy such as 0.1% becomes necessary. The above-mentioned statistical fluctuation of incident X-rays requires the maintenance of such accuracy for producing a meaningful image.

Figure 6:
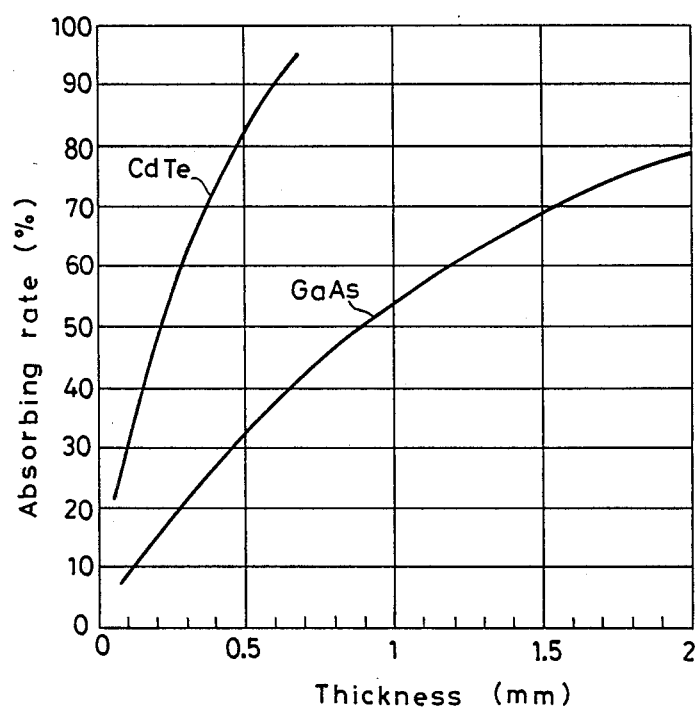
FIG. 6 is a graph showing the relationship between the thickness of one semiconductor element body of the radiation sensitive element and the absorption rate of the elements for an X-ray of 60 keV.

However, if the thickness of the semiconductor crystal chip is decreased, the radiation absorption rate is lowered, thereby lowering radiation sensitivity. FIG. 6 shows the relationship between the semiconductor crystal thickness of CdTe and GaAs versus the absorption rate (%) of a 60 keV X-ray. In general, the effective energy of X-rays used for diagnosis is around 60 keV. When semiconductor crystal thickness is about 0.5 mm, CdTe that has an effective atomic number with respect to photoelectric absorption of about 50, and the absorption rate is about 80%, which is sufficiently large. When the thickness is 0.1 mm, the absorption rate becomes about 30% and is almost actually unusable. Though GaAs has an effective atomic number of about 32, and the absorption rate is about 30% for an 0.5 mm thickness semiconductor crystal chip, (which is smaller than that of CdTe), it is almost actually utilizable. A semiconductor crystal having an effective atomic number smaller than 30 has a poor X-ray absorption rate, and accordingly it is not actually usable because of too low sensitivity to X-rays.

Summarizing the above, a semiconductor crystal chip used as the radiation sensitive element has sufficient sensitivity for absorption of X-rays used in diagnosis when the chip thickness is around 0.5 mm. Furthermore, when the semiconductor crystal chip is thinner than 0.5 mm, the pulse width becomes very narrow.

Figure 7A:
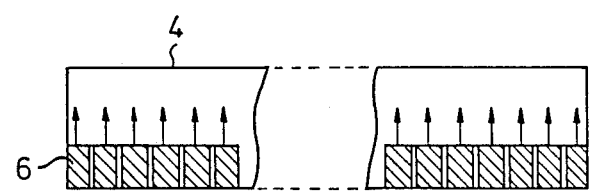
FIG. 7(a) is a schematic plan view of another embodiment.
Figure 7B:
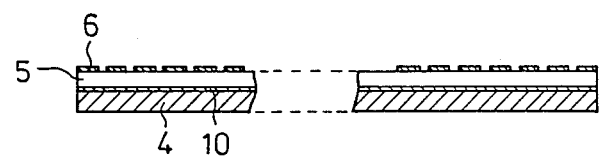
FIG. 7(b) is a sectional front view of the radiation sensitive array of FIG. 7(a).

FIG. 7(a) and FIG. 7(b) show another embodiment of the present invention wherein FIG. 7(a) shows a plan view of a composite structure of semiconductor crystal elements 5 provided on a substrate 4, wherein on a continuous length-wise semiconductor crystal chip 5 and a number of discrete top side electrodes 6 are formed. This type of radiation sensitive element can be manufactured more easily than the embodiment of FIG. 4(a) and FIG. 4(b). The actual configuration of the semiconductor crystal array is not limited to the specific configurations of the above-mentioned embodiments.

Figure 8:
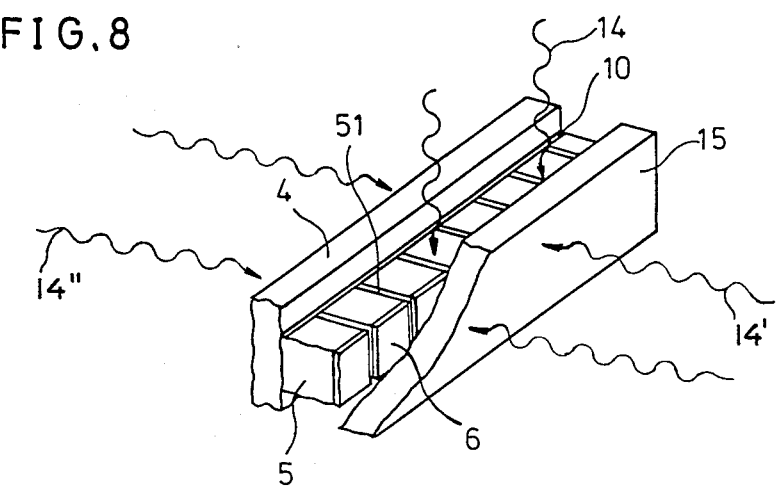
FIG. 8 is a perspective view showing directions of the radiation ray incident on the radiation sensitive element.

The direction of the radiation incident on the semiconductor crystal detector elements is not limited, even though the penetration force of the radiation is dependent on direction. As shown in FIG. 8, metal plate 15 may be used as a filter to adjust the energy of incident radiation. Such a direction sensitive element array may be used to receive incident light 14 and a selected quantum of incident light 14'. This configuration allows the present invention to produce images of high accuracy, and images where the radiation has a short penetration depth. (Each semiconductor crystal chip 5 comprises one detector element corresponding to one picture element.) Alternatively, the radiation may be incident to the semiconductor crystal chips from a direction 14' to come through a metal plate or a like intensity-controlling substance 15. By such selection of the incident direction, intensity of radiation incident to the semiconductor crystal chips 5 may be freely designed, and therefore improvement of sensitivity or resolution may be achieved therewith. In the configuration of FIG. 8, the substrate 4 is located so as to prevent scattered radiation from the side face of the semiconductor crystal chips 5, thereby preventing the degradation of picture quality due to the scattering of the radiation. The plate 15 may be a shield against radiation, and may be independent from the substrate 4, and provided on the opposite side of the semiconductor crystal chips 5 from substrate 4. The substrate 4 as such may also provide shielding against the radiation. When the substrate is the shield, those substrate materials liable to make noise in the semiconductor crystal detector are not desirable. For instance, material which generates high energy X-rays by incident X-rays or β-rays, such as lead or wolfram, or material which becomes radioactive by reason of incident thermal neutrons, (such as, gold, indium or cadmium) should not be used. By using a pulse height analyzer, various scattered rays or other noise signals induced by incident radiation signals can be removed to some extent, but it is necessary to suppress generation of noise as low as possible in order to obtain a high resolution image.

Next, the configuration of the individual semiconductor detector elements will be described. In general, PN junction type electrodes and surface barrier type electrodes may be used for semiconductor detector elements. Both of the electrodes are formed by forming a high resistance layer on the surface thereby to decrease the leakage current produced by the voltage impressed on the detector, to improve the S/N ratio. However, the conventional electrodes of the PN junction type and the surface barrier type have shortcomings such as their tendancy to drift due to accumulation of electron charge at the high resistance layer, or the drifting of the sensitive area due to variations in applied voltage or ambient temperature. Accordingly, in the radiation sensitive elements of the present invention, ohmic contact electrodes are used for the electrodes on both sides of the semiconductor detector elements in order to overcome the above-mentioned shortcomings. In order to utilize ohmic junctions, it is necessary to develop a method for lowering leakage current due to the application of bias-voltage.

Assuming that, the energy given by the radiation quantum incident on the semiconductor detector element is Eg, the average energy to produce one pair of electron-hole pairs in the semiconductor detector element is Wg, and the pulse width of the output pulse signal is t (similar to the equation (1)), then the maximum output current $i_{max}$ generated by the incident radiation rays is given by the following equation (2):

$$i_{max}=(Eg/Wg\cdot t)\times 1.6\times 10^{-19} \qquad (2).$$

When, for instance, incident radiation rays are X-rays of Eg−60 KeV, a CdTe crystal chip is used as the semiconductor detector element, voltage is impressed across a pair of electrodes formed on both faces of the crystal chip, and the chip has a thickness of 0.5 mm, then the pulse width t becomes 0.3 μsec and Wg→4 eV. Accordingly, the above-mentioned equation (2) becomes as follows:

$$i_{max}=8\times 10^{-9} \qquad (3).$$

Our experiments show that a satisfactory S/N ratio is obtainable when the leakage current is under a value as large as 100 times of the value given by the above-mentioned equation (3). As a result, the specific resistance of the semiconductor material is over $10^8$ for such a material of small hole-mobility as CdTe, and on the other hand, for such material as GaAs (which has larger hole-mobility), a satisfactory S/N ratio is obtainable even when using ohmic contact electrodes for both electrodes, even for a specific resistance of over $10^7$.

The specific resistance can be increased by cooling the semiconductor material or by compensating the impurity of the semiconductor of like solutions. However, since it is advantageous to increase the mobility as much as possible, exspecially the hole-mobility which is the characteristic of the semiconductor in making a pulse detector according to the present invention, an intensive compensation of the impurity is not preferable. On the other hand, in order to make the radiography apparatus simple, provision of a complicated refrigeration/cooling apparatus is not preferable. Accordingly, the present invention uses a material having specific resistance of over $10^7$ at room temperature, namely, a semiconductor material having an energy band gap of over 1.3 eV. Thus, materials having an effective atomic number of above 30, having an energy band gap of over 1.3 eV, and furthermore, having hole-mobility of above 50, (such as the above-mentioned GaAs and CdTe) are suitable.

Figure 9:
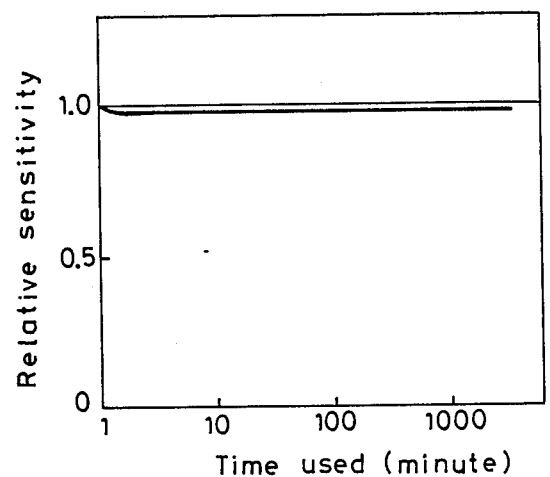
FIG. 9 is a graph showing the stability in relative sensitivity of the semiconductor detector element.
Figure 10:
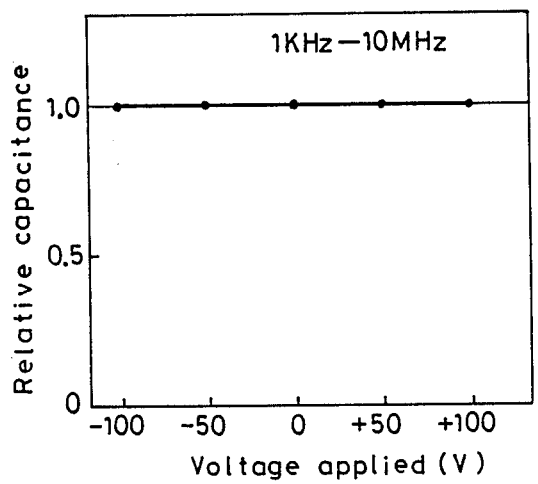
FIG. 10 is a graph showing the voltage dependency of the capacitance of the radiation sensitive element.

FIG. 9 shows the stability in relative sensitivity, (i.e., relative sensitivity versus time) with an applied voltage between the two opposite electrodes of a crystal detection element of CdTe having ohmic contact electrodes. FIG. 10 shows the applied voltage versus reactive capacitance of the same detection element. Quantum of radiation rays absorbed in the semiconductor crystal element are transduced into electric pulses, which are then given to pulse amplifiers 7, and after amplification therein further given to the corresponding pulse counters, and the counted data are further given to corresponding memories. The pulse amplifier, the pulse counter and the memory are provided for each semiconductor crystal detector so that radiation rays incident to semiconductor detector elements of the array (as shown in FIG. 1) can be detected and stored simultaneously. The above-mentioned detections of radiations and storings of the detected and counted information data are successively carried out by stepwisely or gradually moving the array of the semiconductor crystal detectors and the radiation source relative to the object 3. The counted data temporarily stored in the memories are read out in sequence to outside circuitry.

Figure 11:
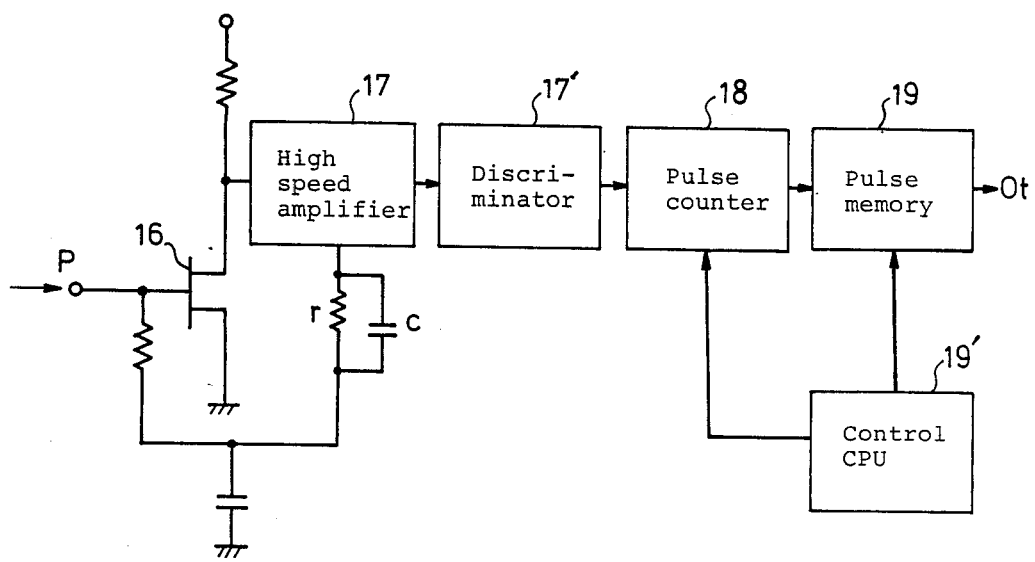
FIG. 11 is a circuit diagram of a concrete embodiment of a circuit to be connected to the semiconductor element of the array.

FIG. 11 shows a circuit diagram of one example of one semiconductor detector element and the electric circuits belonging thereto. The circuit comprises a FET amplifier 16 which is for converting the high impedance pulse signal P into a low impedance pulse signal. The impedance-converted input pulse signal is then given to the amplifier 17, and then given to a discriminator 17', and then given to the pulse counter 18. The counted data from the pulse counter 18 is temporarily stored in the memory 19, the data of which is to be given to a known memory or a known processor. These circuits may be formed on an IC and connected to the semiconductor detector elements.

In general, in radiation pulse measurement, because of the desire to achieve uniformity of height of pulse output of respective radiation sensitive elements regardless of capacitances of the respective sensitive elements, hitherto preamplifiers of the electric charge amplifier type have been mostly used. For a circuit to count pulses at $10^5$ counts per second, such an amplifier is too complicated in circuitry, and is not suitable for a system wherein a number of sets of semiconductor detector elements and pulse amplifiers are provided. Accordingly, the quantum counting radiography apparatus in accordance with the present invention has been improved to include a high gain inverting amplifier having a junction FET of low impedance capacitance as the input stage, and further includes as a pulse amplifier shown in FIG. 12 a preamplifier of the low input impedance type having a feed-back loop with a resistor and a capacitor for providing frequency dependent feed back, and a satisfactory result has been obtained.

Each semiconductor detector element according to the present invention has a very minute configuration, and accordingly the capacitance of each element is below 2 pF. In addition, the electrodes of the semiconductor detector elements are ohmic contact electrodes which are not influenced by impressed voltage or ambient temperature. Accordingly, the semiconductor detector elements provide satisfactory performance by using a voltage-amplification type preamplifier which has high speed response characteristics. But, since each semiconductor detector element has a very high internal resistance (over $10^7 \Omega$), the ordinary voltage-amplifier type of preamplifier could not provide a satisfactory high speed response characteristic. Accordingly, the inventors have developed a special preamplifier with which a good S/N ratio as well as high speed pulse rate counting can be realized, and the preamplifiers can be made in integrated circuit form since the circuit construction is simple.

Figure 12:
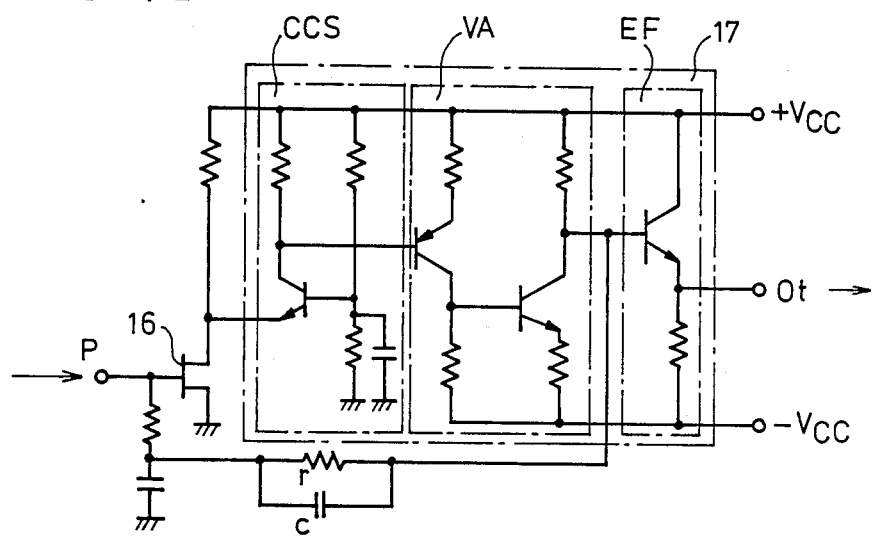
FIG. 12 is a circuit diagram of one example of a low impedance type preamplifier 17 of FIG. 11.

FIG. 12 shows a preferable embodiment of the preamplifier. When the preamplifiers are made on an array-shaped integrated circuit, uniformity of characteristics of junction FETs is an important problem. Accordingly, in this example, a constant current source CCS is adopted as the drain current source of the J-FET 16, so that dispersion characteristics of the J-FET due to dispersion of the gain of the preamplifier is prevented. The output of the J-FET 16 is amplified by a voltage-amplifier VA and is output through an emitter-follower EF.

In general, it is desirable that the number of picture elements in the vertical direction and in the horizontal direction should each be more than 500. On the other hand, time required for radiography should be shorter than 10 seconds at the longest, and hence, the movement of the radiation source and the array of the radiation sensitive elements relative to the object 3 must be within this range of time. As a result, the pulse counting period for one picture element must be under 30 m sec at the longest. That is, in order to obtain an image of high quality radiography, a dynamic range of over 60 dB is necessary, and hence, a counting ability of about $10^5$ pulses per second must be provided. Accordingly, in order to count $10^5$ pulses in 30 m sec, a pulse time resolution power shorter than $0.3\mu$ sec is necessary. The aforementioned semiconductor detector elements have been developed recently to have the performance of such pulse time resolution.

Sensitivity of the array is determined by effective incident cross-section area and the thickness of the sensitive layer, and accordingly, the dispersion of sensitivity is substantially determined by accuracy of cutting on the semiconductor crystal detector elements. Therefore, in order to adjust the sensitivity, trimming of the semiconductor crystal elements is carried out. But as another method, adjusting the sensitivity in the discriminator part of the pulse amplifier, compensation of the count in the counter circuits, or compensation in data processing circuitry can be made. Furthermore, compensation can be made for dispersion of the amplitude of the output pulses between a number of the semiconductor crystal detector elements by making sensitivity adjustment in the pulse amplifier or in the pulse height level discriminator (i.e., comparator).

Figure 13A:
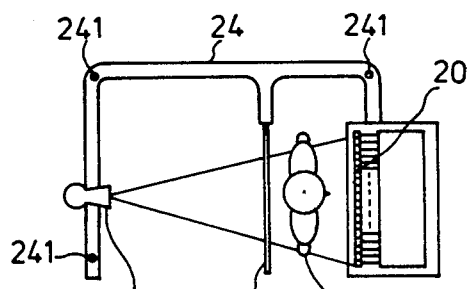
FIG. 13(a) is a plan view showing the location of the slit member used in an actual radiographic system.
Figure 13B:
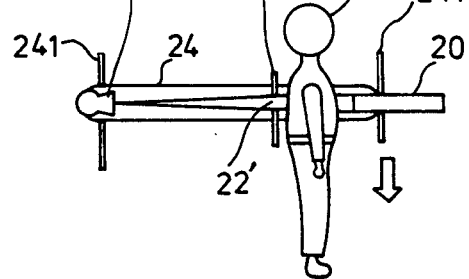
FIG. 13(b) is a side view showing the location of the slit member 22 in the system of FIG. 13(a).

Next, devices for controlling the radiation emission will be described. The devices are designed to decrease the radiation exposure of the objective body to be as low as possible. As shown in FIG. 13(a) (which is a plan view of the quantum counting radiography apparatus in accordance with the present invention), and FIG. 13(b) (which is a side elevation view of the same apparatus), a radiation shield having a slit 22' thereon is disposed between the radiation source 23 and the objective body 21. That is, the radiation shield 22 is fixed on the frame 24, on which the radiation source 23 and the array 20 of the radiation sensitive elements are mounted. As have been described, the semiconductor crystal detector elements of the radiation sensitive elements should be made as thin as possible, for instance under 0.5 mm thick. Accordingly, by accurately disposing the array of radiation sensitive elements in a manner to receive very thin fan-shaped radiation rays irradiated through the slit 22', the amount of exposure of radiation to the objective body 21 can be made as small as possible. Therefore, the width of the slit 22' is designed as narrow as 1 mm. And in order to accurately emit the radiation rays through the slit 22' on the very thin semiconductor crystal chips in the array of the radiation sensitive element, the radiation shield 22 having the slit 22' is rigidly fixed on the frame 24 together with the radiation source 23 and the array 20. By such construction, very thin fan-shaped radiation can be received by the array of thin semiconductor crystal chips of the radiation sensitive elements.

As another configuration, an accurate irradiation of the radiation sensitive elements array through the slit 22', may be provided by co-operatively moving the slit 22' and the array 20 while fixing the radiation beam source 23. In such a configuration, accurate control of the array can be made by disposing additional radiation sensitive elements on both ends of the array for detecting the relative positional relationships. Thereby, moving the array may be servomechanically controlled by utilizing the position detection information from the additional radiation sensitive elements.

FIG. 14(a), which is a plan view, and FIG. 14(b), which is a side view of another embodiment, show a configuration in which the radiation beam source 23 and the array 20 of the radiation sensitive elements are moved in the plane of the fan-shaped radiation rays. This configuration, as is known, can produce tomographic image information.

The above-mentioned embodiments reveal that, by using a 500 bit array of radiation sensitive elements to receive fan-shaped radiation rays of 60 KeV and 1 mR X-rays, a clear X-ray image was obtained. And the obtained X-ray image has several tens of times higher sensitivity than the conventional X-ray photograph using silver salt or conventional pulse counting or electric charge or galvanic apparatus using an array of xenon discharge tubes. Furthermore, the quantum counting radiography in accordance with the present invention can produce images immediately after emitting the radiation in contrast to the conventional silver salt photographic method or thermal luminescence method which takes a considerable time for developing and fixing the images. The quantum counting radiography method and apparatus in accordance with the present invention can of course be applied to computer tomography. Experiments have shown that when the radiographic image is obtained by using $10^6$ count pulses per one picture element, satisfactory contrast is obtainable thereby enabling delicate differences in soft tissues (such as cancer tissue in the surrounding normal tissues) to be obtained. Such differentiation has been impossible to obtain with the conventional silver salt photography method. Experiments have shown that a cancer focus of a size of within 1 cm can be detected in accordance with the present invention.

What is claimed is:

1. A radiation quantum-counting method of radiography comprising the steps of:
    (a) emitting quanta of radiation from a radiation source toward an objective body;
    (b) detecting individual radiation quantum passing through said objective body, and providing a pulse signal for each such detected quantum, said detecting step including the step of receiving said radiation quanta on a plurality of semiconductor, radiation sensitive elements, each element having first and second electrodes disposed on opposite faces of a semiconductor material which is substantially 0.1–0.5 mm thick, said semiconductor material having an effective atomic number greater than 30 and an energy band gap greater than 1.3 eV, each said element providing said pulse signal when it detects one of said radiation quantum, said elements providing a plurality of pulse signals;
    (c) amplifying said pulse signals with a plurality of pulse amplifiers to provide amplified pulse signals, each amplifier coupled to a respective one of said radiation sensitive elements;
    (d) counting the amplified pulse signals provided by said pulse amplifiers to provide pulse number data;
    (e) producing radiographic image signals from said pulse number data;
    (f) storing said pulse number data in memory means;
    (g) moving said objective body relative to said radiation source and said radiation sensitive elements; and
    (h) repeating steps (a)–(f) after step (g) is performed for providing plural sets of said radiographic image signals comprising two-dimensional signals having quantum number data of image gradation therein.

2. A method according to claim 1 further including the step of selectively shielding said radiation from said objective body by positioning a radiation shield between said radiation source and said body, said shield having a slit therein to cause a fan-shaped radiation pattern to strike said body.

3. A method according to claim 2 further including the steps of:
    arranging said radiation sensitive elements in a linear array to cause said fan-shaped pattern to strike said linear array; and
    positioning said linear array, said radiation source, and said radiation shield on a composite structure, said structure being in movable relationship relative to said body.

4. A method according to claim 1 wherein said counting step includes the step of counting, in less than 30 msec, pulse signals to form one pixel of a radiological image derived from said radiographic image signals.

5. A method according to claim 1 further including the step of adjusting the sensitivity of said radiation sensitive elements.

6. A method according to claim 1 further including the step of adjusting the sensitivity of said radiation sensitive elements with computing means coupled to receive said pulse signals.

7. A method according to claim 1 wherein said detecting step includes the step of receiving said radiation on CdTe radiation sensitive elements.

8. A method according to claim 1 wherein said detecting step includes the step of receiving said radiation on GaAs radiation sensitive elements.

9. A radiation-quantum counting apparatus comprising:
   radiation source means for emitting quanta of radiation toward an objective body;
   detector means for detecting individual radiation quantum passing through said objective body, and generating a pulse signal for each detected quantum, said detector means including a plurality of semiconductor, radiation sensitive elements, each element having first and second electrodes disposed on opposite faces of a semiconductor material which is substantially 0.1–0.5 mm thick, said semiconductor material having an effective atomic number greater than 30 and an energy band gap greater than 1.3 eV, each said element providing said pulse signal when it detects one of said radiation quantum, said elements providing a plurality of pulse signals; and
   means for causing relative movement between said objective body and said radiation source means.

10. Apparatus according to claim 9 further including:
    a plurality of pulse amplifiers, each coupled to a respective one of said radiation sensitive elements, for amplifying said pulse signals;
    a plurality of pulse counters, each coupled to a respective one of said pulse amplifiers, for counting the amplified pulse signals and providing pulse number data related to the counted pulse signals;
    memory means for storing said pulse number data; and
    control means for causing said memory means to store a sequence of sets of pulse number data, each set corresponding to a different relative position between said radiation source and said body.

11. Apparatus according to claim 10 wherein each pulse counter counts, in less than 30 msec, pulse signals to form one pixel of a radiological image derived from said pulse number data.

* * * * *